United States Patent
Koby et al.

(10) Patent No.: US 7,645,250 B2
(45) Date of Patent: Jan. 12, 2010

(54) REVERSIBLE WRIST AND THUMB SUPPORT

(76) Inventors: Aurelia Koby, 4461 Ocean Blvd., San Diego, CA (US) 92109-3926; Ian MacMorran, 886 Cordova St., San Diego, CA (US) 92107-4222

( * ) Notice: Subject to any disclaimer, the term of this patent is extended or adjusted under 35 U.S.C. 154(b) by 590 days.

(21) Appl. No.: 11/141,952

(22) Filed: Jun. 1, 2005

(65) Prior Publication Data

US 2005/0273030 A1  Dec. 8, 2005

Related U.S. Application Data

(60) Provisional application No. 60/576,396, filed on Jun. 2, 2004.

(51) Int. Cl.
*A61F 5/00* (2006.01)
*A61F 13/00* (2006.01)
(52) U.S. Cl. .................... 602/21; 602/5; 602/20; 602/22; 602/60; 602/61
(58) Field of Classification Search .......... 2/158–161.8; 602/5, 20–22, 60–64; 128/877–880
See application file for complete search history.

(56) References Cited

U.S. PATENT DOCUMENTS

| | | | |
|---|---|---|---|
| D259,955 S * | 7/1981 | Helferich | D24/190 |
| 4,658,441 A | 4/1987 | Smith | |
| 4,862,877 A | 9/1989 | Barber | |
| 4,953,568 A | 9/1990 | Theisler | |
| 5,356,371 A | 10/1994 | Hubbard | |
| 5,561,856 A | 10/1996 | Pesco | |
| 5,682,611 A | 11/1997 | Kline | |
| 5,713,836 A | 2/1998 | O'Keefe | |
| 5,746,707 A | 5/1998 | Eck | |
| D405,180 S | 2/1999 | Reina | |
| 5,873,130 A * | 2/1999 | Lafferty | 2/16 |
| 6,165,148 A | 12/2000 | Carr-Stock | |
| 6,213,969 B1 * | 4/2001 | MacMorran et al. | 602/64 |
| 6,694,523 B2 * | 2/2004 | Hurst | 2/161.7 |
| 2003/0191421 A1 * | 10/2003 | Weaver et al. | 602/22 |
| 2005/0197609 A1 * | 9/2005 | Mills | 602/21 |

FOREIGN PATENT DOCUMENTS

EP            014348 A1 *  6/1995

* cited by examiner

*Primary Examiner*—Kim M Lewis
(74) *Attorney, Agent, or Firm*—Duane Morris LLP

(57) ABSTRACT

A reversible wrist and thumb support is formed of a sleeve of resiliently stretchable material and includes an optionally detachable thumb support coupled to the sleeve. The thumb support includes a plurality of removable battens formed of a semi-rigid material and disposed along the posterior of a wearer's thumb. A resiliently deformable support pad is disposed on an underside of the splint and a removable stiffening semi-rigid batten that optionally includes padded surfaces, is disposed in a pocket on the top side of the support. The reversible wrist and thumb support may be worn on either the wearer's left or right hand, and the battens need not be removed when the reversible wrist and thumb support is turned inside-out.

23 Claims, 4 Drawing Sheets

REVERSIBLE WRIST AND THUMB SUPPORT

RELATED APPLICATION

This application is related to, and claims priority of U.S. provisional application Ser. No. 60/576,396 filed Jun. 2, 2004, the contents of which are hereby incorporated by reference as if set forth in its entirety.

FIELD OF THE INVENTION

The present invention relates to a reversible wrist and thumb support.

BACKGROUND

Repetitive motion injuries to the wrist and/or thumb are a steadily increasing problem among workers who perform repetitive tasks generally, and among typists and other keyboard workers in particular. A newly emerging problem is repetitive motion injuries, particularly those associated with the thumb, caused by the use of pda's (personal data assistants). For example, "Blackberry thumb" is a newly coined expression for such an injury. These injuries include carpal tunnel syndrome (CTS), deQuervains and other injuries. The pain resulting from such injuries and from arthritis, tendonitis and other hand fatigue can be excruciating, very difficult to treat, and debilitating. Loss of productivity due to these ailments and injuries among keyboard workers and even occasional keyboard wearers is estimated to be in the billions of dollars annually. Orthopedic restraint devices of many types and styles are commercially available. These devices, of course, have various degrees of effectiveness. Mere restrained movement is a primary treatment for any joint injury or joint pain. While restraint addresses such injuries and pain, there is a countervailing need to accommodate some movement in a working environment. Therefore, the orthopedic restraint devices must strike a compromise between maximum restraint and some mobility i.e., they should provide comfort and retain a significant stiffness that will urge but not force the wearer's wrist and thumb to neutral positions. The present invention addresses these concerns and provides such restraint as well as adjustable comfort with a desirable degree of mobility.

U.S. Pat. No. 6,213,969 to the applicant inventors, describes a glove/sleeve that serves as a carpal tunnel support. The contents of U.S. Pat. No. 6,213,969 are hereby incorporated by reference, as if set forth in their entirety. The carpal tunnel support of U.S. Pat. No. 6,213,969, however, does not provide support for the wearer's thumb, and therefore does not address or provide any intervention or remedy for the aforementioned injuries and maladies that can affect the joints of the wearer's thumb.

It would therefore be desirable to provide a wrist and thumb support that is easily put on, comfortable to the wearer, and provides a suitable compromise between restraint to prevent or cure repetitive motion injuries, and movement to allow the wearer to perform various operational functions.

Many orthopedic restraint devices are of fixed configuration, for example splints and other rigid portions are fixed in position, i.e., they are not removable or adjustable. In order to accommodate various wearers, uses and symptoms, it would be desirable to produce a wrist and thumb support with removable features. Cost savings are always a prominent consideration of a wearer/consumer. It would therefore be further desirable to provide a wrist/thumb support, especially one with rigid or semi-rigid support members, that is reversible and can be worn interchangeably on either of the wearer's hands.

These and other objectives are met by the invention summarized and described below.

SUMMARY OF THE INVENTION

To address these and other needs, and in view of its purposes, the present invention provides a reversible wrist and thumb support comprising a sleeve having opposed open ends, formed of a resiliently stretchable material and for receiving a wearer's wrist and palm. Coupled to the sleeve is a thumb support formed of a resiliently stretchable material. The thumb support includes a plurality of battens arranged in parallel to one another and the wearer's thumb, and disposed along the posterior of the wearer's thumb. Each of the battens is formed of a semi-rigid material and the wrist and thumb support is interchangeably wearable on each of the wearer's left and right hand.

In another aspect, the invention provides a reversible wrist and thumb support comprising a sleeve having opposed open ends, formed of a resiliently stretchable material and for receiving a wearer's wrist and palm. A thumb support is detachably coupled to the sleeve and includes a duality of removable battens arranged in parallel and on opposed sides of a line that bisects the posterior of the wearer's thumb. Each of the battens is formed of a semi-rigid material and includes opposed padded surfaces. The wrist and thumb support is reversibly wearable on each of the wearer's left and right hand.

In another aspect, a reversible wrist and thumb support is provided. It includes a sleeve having opposed open ends, formed of a resiliently stretchable material and for receiving a wearer's wrist and palm. A thumb support includes a plurality of removable battens arranged along a posterior of the wearer's thumb, parallel to one another and the wearer's thumb. Each of the battens is formed of a semi-rigid material and includes opposed padded surfaces. A deformable pad is disposed on an underside of the sleeve to space a heel of the wearer's palm above the surface upon which the wearer's arm rests. The pad may be filled with a plurality of LDPE beads. A splint batten is received within a top portion of the reversible wrist and thumb support to resist upward movement of the wearer's hand. The reversible wrist and thumb support is wearable on each of a wearer's left and right hands.

BRIEF DESCRIPTION OF THE DRAWING

The present invention is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawing.

DETAILED DESCRIPTION

A working wrist and thumb support is provided to restrain the wrist joint and thumb to therapeutically advantageous neutral positions while allowing sufficient movement of the thumb and fingers to enable the wearer to operate various devices such as a keyboard. The wrist and thumb support of the invention restrains the wrist and thumb in comfortable, neutral positions to treat and prevent carpal tunnel syndrome, deQuervains syndrome, arthritis, tendonitis, hand fatigue, and various other repetitive motion ailments of the hand, wrist and thumb. The therapeutic wrist and thumb support preferably includes semi-rigid, removable splinting features and allows sufficient hand and finger movement for the wearer to operate various keyboards, a mouse and track ball combination, a laptop computer, a calculator, various electronic games and gaming devices, handheld devices such as Blackberrys or other pda's, and also to perform various other operations and operate various types of equipment and machinery.

The general form of the support is a main fabric sleeve with opposed open ends. It includes an aperture for the wearer's fingers and a thumb support advantageously formed of the same fabric as the main sleeve. The support includes a wrist splint in the form of a stiffening and semi-rigid batten removably received in a pocket formed at the top of the central sleeve of the support and over the back of the wearer's hand and wrist. The pocket and wrist batten may run essentially the entire length of the main sleeve section or this splinting feature may be shorter than the main sleeve. The support further includes a thumb splint consisting of at least two removable semi-rigid battens positioned to the posterior of the wearer's thumb. In one embodiment, the wrist and thumb support includes a resiliently deformable wrist support pad integrally formed as a bottom pillow-type portion of the support. The wrist and thumb support may be turned inside-out and may therefore be worn on either hand.

The wrist and thumb support of the present invention incorporates various features of the wrist support disclosed in U.S. Pat. No. 6,213,969 by the applicant inventors. U.S. Pat. No. 6,213,969 describes a wrist support with an opening for the wearer's thumb to extend through and the present invention adds a thumb support as shown in FIGS. 1 and 3-5.

Figure 1:
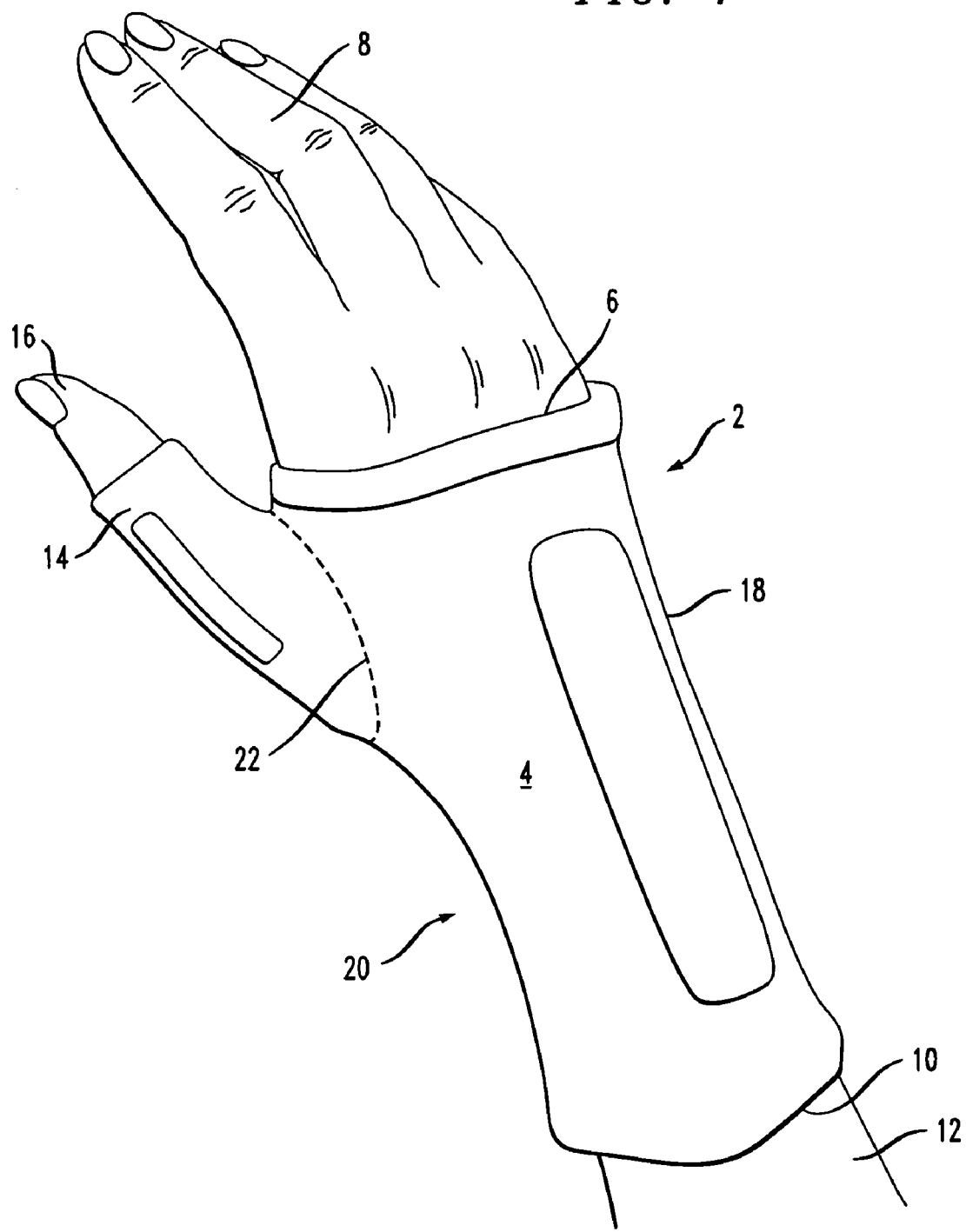
FIG. 1 is a perspective view of an exemplary wrist and thumb support of the invention.

FIG. 1 shows wrist and thumb support 2, which includes main fabric sleeve 4 that receives a portion of the wearer's arm, wrist and palm. Main fabric sleeve 4 includes forward opening 6 which accommodates the wearer's hand 8 and rearward opening 10 that accommodates the wearer's arm 12 Wrist and thumb support 2 include upper portion 18 and lower portion 20. Main fabric sleeve 4 is advantageously formed of a fabric that is resiliently stretchable. Various fabrics such as cotton-lycra or other spandex materials may be used. The main sleeve material is breathable and resilient in orthogonal directions and can provide different degrees of spring/stretching strength. Wrist and thumb support 2 is advantageously formed of a washable material. Wrist and thumb support 2 includes thumb support 14 that accommodates the wearer's thumb 16. thumb support 14 may be advantageously integrally formed of the same resiliently stretchable material as main fabric sleeve 4, and provides a splint that includes at least two removable battens disposed in corresponding pockets (and shown in subsequent figures). thumb support 14 may be seamless at intersection 22 formed between thumb support 14 and main fabric sleeve 4. In other embodiments, thumb support 14 may be formed of a different material that provides more or less support and in yet another exemplary embodiment, it may be detachable. A hook and loop-type fastener such as VELCRO™ or other detachable adhesive materials may be used to couple thumb support 14 to main fabric sleeve 4. thumb support 14 extends at least past the metacarpal phalangel joint of the thumb and in one embodiment may also receive the inter-phalangel joint of thumb 16. By turning the reversible wrist and thumb support 2 of the invention inside out, wrist and thumb support 2 may be worn on, the wearer's other hand with thumb support 14 receiving the wearer's left thumb when worn on the left hand and the wearer's right thumb when worn on the right hand. A comfortable cotton-like or other material or lining may be disposed on each of the opposed sides of wrist and thumb support 2 to provide comfort when worn on either hand.

Figure 2:
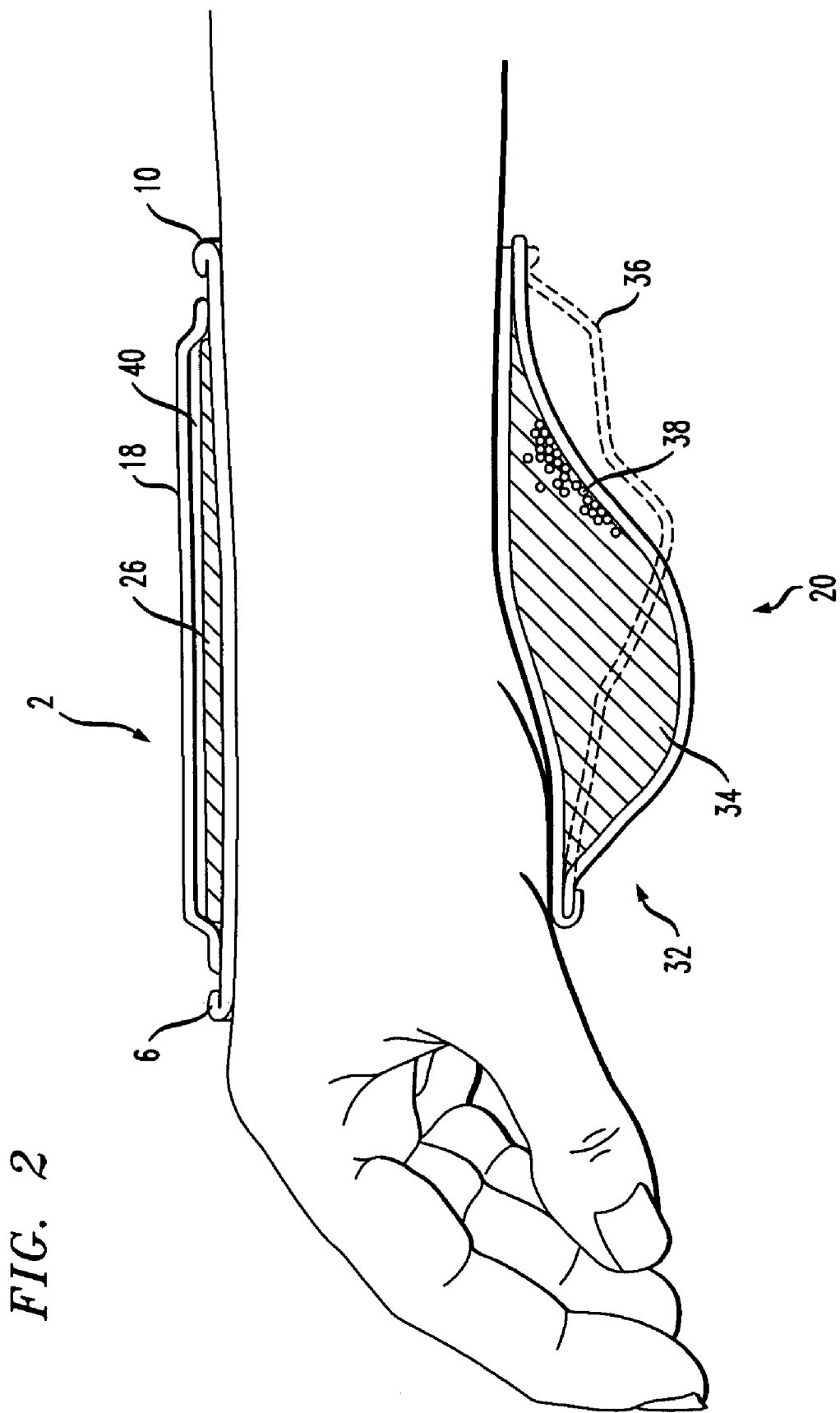
FIG. 2 is a cross sectional view of portions of an exemplary wrist and thumb support of the invention.
Figure 3:
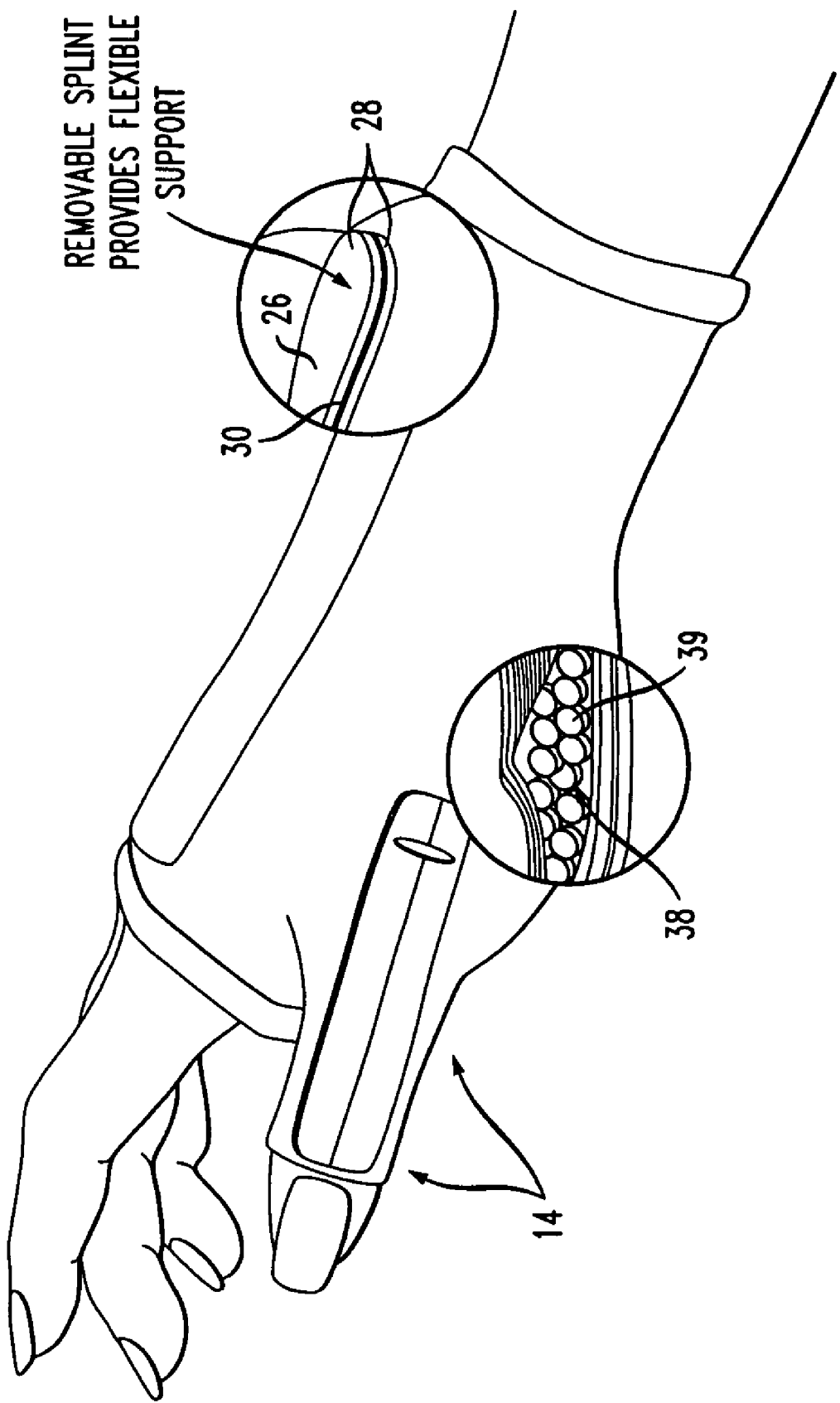
FIG. 3 is a perspective view of an exemplary wrist and thumb support including cut-away portions of features of the wrist and thumb support.

FIG. 2 shows portions of wrist and thumb support 2 in cross-section. Splint batten 26 is received in pocket 40 on upper portion 18. Batten 26 is removable and forms a wrist splint. Removable batten 26 is preferably formed of a semi-rigid material such as plastic, polymeric material, thin wood or other suitable semi-rigid materials that provides support but are somewhat flexible. One difficulty in achieving the therapeutically advantageous neutral position is that this position is inexactly defined and can be different for each sufferer, or different for the left and right hands of a single sufferer. Small angular movement or adjustments can be the difference between a fully neutral, relaxed posture and a fully contacted, painful posture of the wrist. The semi-rigid nature of the wrist splint (batten 26) accommodates various degrees of restraints and support and allows the wearer to find, by experimentation, the neutral position that is most effective in relieving pain. Batten 26 is removably inserted into sleeve 40 through opening 44 (shown in FIG. 4) to form the wrist splint and may include a cushioning or padding material such as foam, padding or a gel pocket on at least one side. The cushioning material advantageously faces the wearer's hand. The cushioning material and semi-rigid batten 26 is shown in more detail in FIG. 3 which shows batten 26 including semi-rigid core 30 with cushioning material 28 on each of opposed sides. In this embodiment with cushioning material 28 on each of opposed sides, either side may face inwardly towards the wearer's wrist, batten 26 need not be removed when the reversible wrist and thumb support 2 is turned inside-out to be worn on the wearer's opposite hand.

Returning to FIG. 2, deformable palm pad 32 is formed on underside 20 of wrist and thumb support 2. This deformable pad accommodates a plurality of ergonomically favorable positions. Deformable palm pad 32 is an optional feature and may be absent from some embodiments. Deformable palm pad 32 is resiliently deformable such as shown in FIG. 2 which shows deformable palm pad 32 in two different configurations such as may be achieved when the wearer's wrist rests on various underlying surfaces and structures. First configuration 34 differs from second configuration 36. Deformable palm pad 32 spaces the heel of the wearer's palm above the work or other surface upon which the wearer's arm rests.

Deformable palm pad 32 may be formed of rubber or filled with a gel. In one exemplary embodiment, deformable palm pad 32 is filled with a granular filling material 38 that may be a plurality of small, tightly packed pellets or beads, hereinafter referred to collectively as beads. Beads 39 are shown in the cut-away portion of FIG. 3 that shows filling material 38. Beads 39 may be oval, elliptical, round, disc or egg-shaped, without sharp or rough edges and with a completely smooth exterior. The exemplary beads 39 or other filling material 38 is tightly packed in a corresponding pocket that forms deformable palm pad 32, to a sufficiently high density so that deformable palm pad 32 is moldable as the beads smoothly redistribute responsive to the underlying structure and the position of the wearer's hand and wrist. The packing and configuration may be so as to provide a resiliency to deformable palm pad 32.

Filling material 38 may be tightly packed within the pocket to provide complete and smooth moldability. Filling material 38 may be advantageously formed of thermal storage material capable of maintaining a reduced temperature for an extended period of time. By reduced temperature, it is meant that the temperature of the thermal storage material is lower than that of the ambient environment. The reduced temperature may be a temperature at or below 32° F., a temperature at or below 40° F., or any temperature that is less than room temperature. Wrist and thumb support 2 may be stored in a household refrigerator or freezer, for example to cool the thermal storage and material. In one exemplary embodiment, ergoBeads™ may be used as filler material 38. Since filling material 38 is advantageously formed of a population of small beads 39 with tiny air pockets between the beads, it provides a more comfortable soothing cool than the freezing cold sensation such as provided by ice or gel. As opposed to ice which has a temperature of 32° F. or lower, filling material 38 may be maintained at reduced temperatures greater than 32° F. Deformable palm pad 32 has a smooth conformal nature that is more comfortable than the lumpy surface of an ice bag which includes sharp or hard edges that may provide pressure points of extreme cold. According to the embodiment in which filling material 38 is a thermal storage material, the thermal storage material may additionally or alternatively be chosen to retain heat and provide soothing warmth. Various thermal storage materials may be used.

Exemplary beads 39 of filling material 38 have smooth exterior surfaces. In an exemplary embodiment, beads 39 may be formed of low density polyethylene ("LDPE") and may be natural or semi-clear white in color. They may be injection molded or extrusion type LDPE particles. Beads 39 are free of sharp edges and include a surface that has an average surface roughness of less than 100 nanometers in one exemplary embodiment enabling the beads to slide easily and freely against each other. The beads' surface may advantageously be polished to enhance smoothness. A coating may optionally be added to filling material 38, in particular coating the surfaces of beads 39. The coating may be a powdery coating formed of a mold-release agent such as an amide, or other materials that provide lubrication. Beads 39 maintain their surface smoothness and the easy deformability of deformable palm pad 32 is retained at a range of suppressed temperatures below 32° F.

Exemplary illustrated disc shaped beads 39 may include a pair of opposed round or oval surfaces and a length chosen to be less than or equal to 4.5 millimeters in one exemplary embodiment. Beads 39 may include dimensions of 3 millimeters×4.5 millimeters×2 millimeters and a density of 0.910 to 0.935 grams per cubic centimeter but other sizes and densities may be used in other exemplary embodiments, however. In another exemplary embodiment, beads 39 may include dimensions of about 6 millimeters×4 millimeters×3 millimeters. The exemplary dimensions provided are illustrative but not restrictive of the bead dimensions as other dimensions may be used in other exemplary embodiments. The beads may optionally include at least one dimple. Filler material 38 is packed tightly enough so that deformable palm pad 32 is deformable or moldable as the beads redistribute responsive to contact surfaces and positioning by the wearer. When deformable palm pad 32 is in contact with a wearer, a gentle massaging action is created by filling material 38 when pressure such as a gentle rolling action is applied to the opposed side of deformable palm pad 32.

Figure 4:
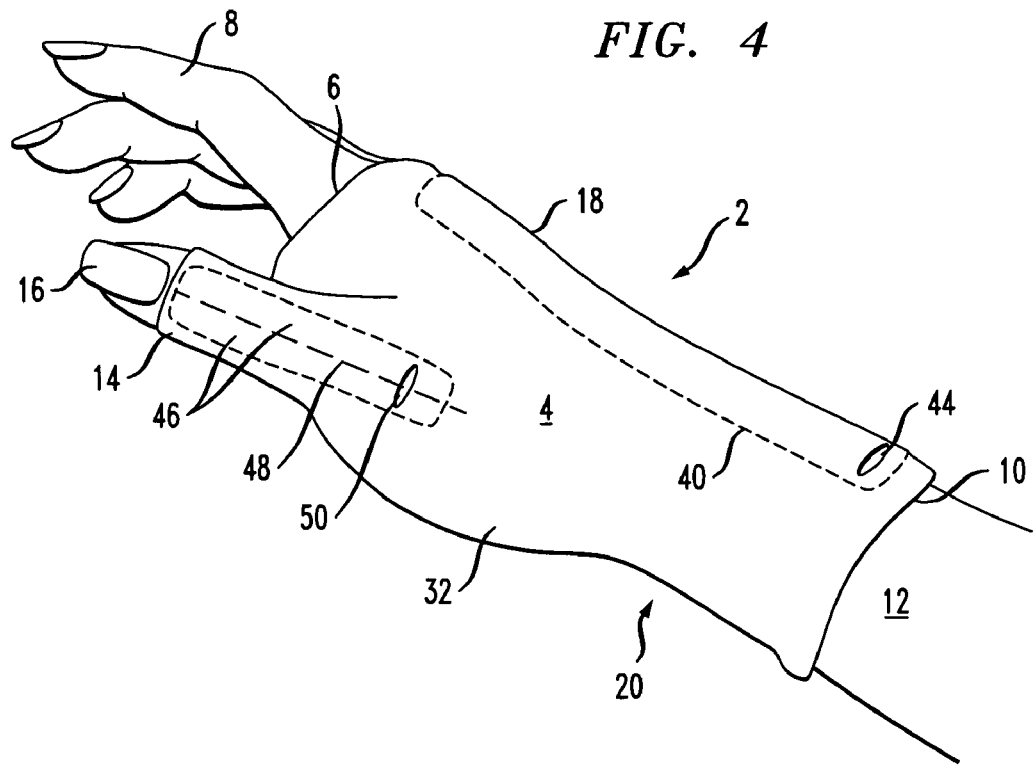
FIG. 4 is a perspective view of an exemplary wrist and thumb support of the invention.
Figure 5:
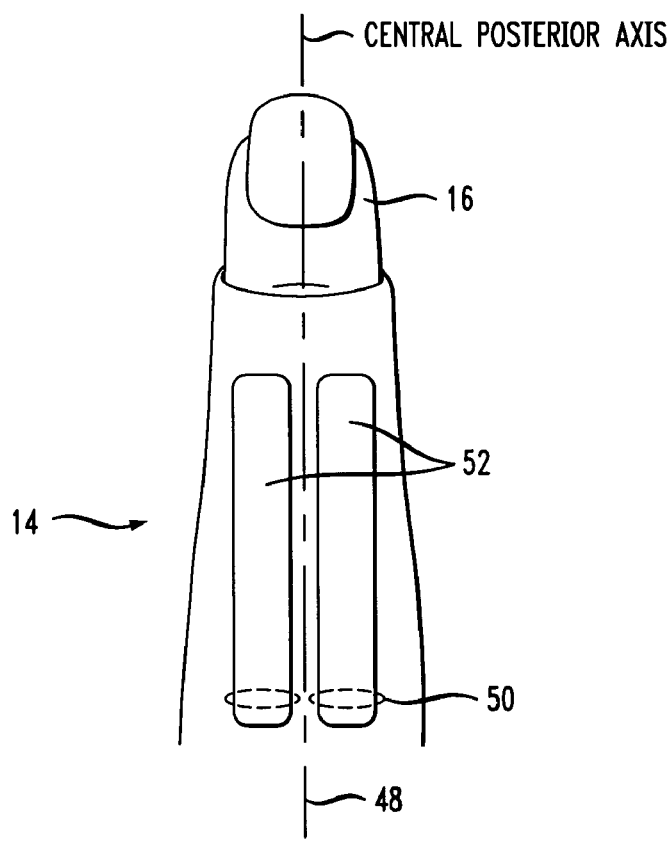
FIG. 5 is a top view of an exemplary thumb support of the invention.

FIG. 4 illustrates additional features of wrist and thumb support 2. Slit 44 accommodates insertion of splint batten 26 (not visible in FIG. 4) in pocket 40. thumb support 14 includes pockets 46 into which thumb battens (not visible in FIG. 4) are inserted through slit 50. In the exemplary embodiments shown in FIGS. 4 and 5, thumb battens 52 are received in posterior pockets 46 that are positioned adjacent and on opposed sides of central axis 48 that bisects the wearer's thumb. thumb battens 52 are parallel to each other and to the wearer's thumb. Although illustrated as being substantially adjacent, thumb battens 52 may be spaced slightly apart in other embodiments. thumb battens 52 are removable through slit 50. In another embodiment, three thumb battens that extend parallel to one another and the wearer's thumb 16 may be received in corresponding posterior pockets formed on thumb support 14. thumb battens 52 are also semi-rigid and provide the benefits described above in conjunction with batten 26. Removable thumb battens 52 may be formed of plastic, various polymers, wood or other suitable semi-rigid materials. thumb battens 52 may include cushioning or padding on either or both of the opposed sides. In another embodiment, cushioning may not be used. Slight bending of wearer's thumb 16 is achievable without discomfort because of the semi-rigid nature and the advantageous positioning of thumb battens 52 of the multiple-piece thumb splint when no thumb batten is positioned directly behind central axis 48 of wearer's thumb 16. Battens 52 may extend essentially along the entire posterior of wearer's thumb 16 or only a portion of wearer's thumb 16.

Although the invention has been described in terms of exemplary embodiments, it is not limited thereto. The preceding merely illustrates the principles of the invention. It will thus be appreciated that those skilled in the art will be able to devise various arrangements which, although not explicitly described or shown herein, embody the principles of the invention and are included within its spirit and scope. For example, rigid battens such as formed of metal, may be used as wrist and/or thumb battens in other exemplary embodiments.

Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A reversible wrist and thumb support comprising:
   a resiliently stretchable sleeve having opposed open ends and for receiving a wearer's wrist and palm, and
   a resiliently stretchable thumb support coupled to said sleeve and including a plurality of battens adapted to be disposed parallel to one another and to a wearer's thumb and disposed along a posterior of said wearer's thumb, each of said battens formed of a semi-rigid material, and
   said wrist and thumb support being reversible and wearable on each of a wearer's left hand and right hand.

2. The reversible wrist and thumb support as in claim 1, wherein said plurality of battens comprise two removable battens disposed adjacent one another and on opposed sides of a central axis that generally bisects said wearer's thumb.

3. The reversible wrist and thumb support as in claim 1, wherein said plurality of battens comprise three removable battens including a first batten disposed along a line bisecting said wearer's thumb and further battens disposed on opposed sides of said first batten.

4. The reversible wrist and thumb support as in claim 1, wherein said thumb support is strapless and said thumb support and said sleeve are formed of a continuous piece of a resiliently stretchable material and an intersection of said sleeve and said thumb support is seamless.

5. The reversible wrist and thumb support as in claim 1, wherein at least one of said plurality of battens is padded.

6. The reversible wrist and thumb support as in claim 1, wherein said battens are adjoining.

7. The reversible wrist and thumb support as in claim 1, wherein said battens are removable and said thumb support includes a slit therein to accommodate insertion and removal of said plurality of removable battens.

8. The reversible wrist and thumb support as in claim 1, further comprising a semi-rigid splint batten joined to an upper portion of said sleeve to resist upward movement of said wearer's hand.

9. The reversible wrist and thumb support as in claim 8, wherein said splint batten is removable and said upper portion includes an opening in said resiliently stretchable material to accommodate insertion and removal of said splint batten.

10. The reversible wrist and thumb support as in claim 8, wherein at least one side of said splint batten includes a cushioning material formed thereon.

11. The reversible wrist and thumb support as in claim 1, further comprising a deformable pad disposed on an underside of said sleeve, to space a heel of said wearer's palm above a work surface upon which said wearer's arm rests.

12. The reversible wrist and thumb support as in claim 11, wherein said pad comprises a pocket formed integrally within said sleeve and is filled with gel.

13. The reversible wrist and thumb support as in claim 11, wherein said pad comprises a pocket formed integrally within said sleeve and filled with a plurality of beads composed of low density polyethylene (LDPE).

14. The reversible wrist and thumb support as in claim 13, wherein said beads are formed of a thermal storage material capable of retaining a reduced temperature.

15. The reversible wrist and thumb support as in claim 1, wherein said semi-rigid material comprises plastic.

16. The reversible wrist and thumb support as in claim 1, wherein said resiliently stretchable material comprises cotton lycra or a further spandex material.

17. The reversible wrist and thumb support as in claim 1, wherein said sleeve and said thumb support are each formed of a resiliently stretchable material that includes opposed fabric surfaces.

18. The reversible wrist and thumb support as in claim 1, wherein said thumb support is detachably coupled to said sleeve.

19. A reversible wrist and thumb support comprising:
   a sleeve having opposed open ends, formed of a resiliently stretchable material and for receiving a wearer's wrist and palm, and
   a thumb support detachably coupled to said sleeve including at least a batten arranged parallel to said wearer's thumb, each of said battens formed of a semi-rigid material and including opposed padded surfaces,
   said reversible wrist and thumb support being reversibly wearable on each of a wearer's left hand and right hand.

20. The reversible wrist and thumb support as in claim 19, wherein said thumb support is resiliently stretchable and said at least one batten comprises a duality of removable battens disposed on opposed sides of a line bisecting said wearer's thumb.

21. A reversible wrist and thumb support comprising:
   a sleeve having opposed open ends, formed of a resiliently stretchable material and for receiving a wearer's wrist and palm, and
   a thumb support formed of said resiliently stretchable material and including a plurality of removable battens arranged along a posterior of said wearer's thumb, in parallel to one another and said wearer's thumb, each of said battens formed of a semi-rigid material and including opposed padded surfaces,
   a deformable pad adapted to be arranged on an underside of said sleeve to space a heel of said wearer's palm above a work surface upon which said wearer's arm rests, said pad filled with a plurality of LDPE beads; and
   a splint batten received within a top portion of said reversible wrist and thumb support to resist upward movement of said wearer's hand,
   said reversible wrist and thumb support being wearable on each of a wearer's left hand and right hand.

22. A reversible wrist and thumb support comprising:
   a resiliently stretchable sleeve having opposed open ends and for receiving a wearer's wrist and palm, and
   a resiliently stretchable thumb support coupled to said sleeve and including a plurality of battens arranged parallel to one another and to a wearer's thumb and adapted to be disposed along a posterior of said wearer's thumb, and
   said wrist and thumb support being reversible and wearable on each of a wearer's left hand and right hand, said sleeve formed of a resiliently stretchable fabric having opposed first and second surfaces, said first surface adapted to be disposed externally when said wrist and thumb support is worn on said user's left hand and said second surface adapted to be disposed externally when said wrist and thumb support is worn on said user's right hand.

23. The reversible wrist and thumb support as in claim 22, wherein each of said battens is farmed of a rigid material.

* * * * *

UNITED STATES PATENT AND TRADEMARK OFFICE
CERTIFICATE OF CORRECTION

PATENT NO. : 7,645,250 B2  Page 1 of 1
APPLICATION NO. : 11/141952
DATED : January 12, 2010
INVENTOR(S) : Koby et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1114 days.

Signed and Sealed this

Sixteenth Day of November, 2010

David J. Kappos
*Director of the United States Patent and Trademark Office*